US007190987B2

(12) United States Patent
Lindekugel et al.

(10) Patent No.: US 7,190,987 B2
(45) Date of Patent: Mar. 13, 2007

(54) NEONATAL BOOTIE WRAP

(75) Inventors: Eric Lindekugel, Fort Collins, CO (US); Lily Anjanette Medina, Longmont, CO (US); Dena Raley, Louisville, CO (US)

(73) Assignee: Datex-Ohmeda, Inc., Louisville, CO (US)

( * ) Notice: Subject to any disclaimer, the term of this patent is extended or adjusted under 35 U.S.C. 154(b) by 896 days.

(21) Appl. No.: 10/394,525

(22) Filed: Mar. 21, 2003

(65) Prior Publication Data
US 2003/0181799 A1 Sep. 25, 2003

Related U.S. Application Data

(60) Provisional application No. 60/366,330, filed on Mar. 21, 2002.

(51) Int. Cl.
*A61B 5/00* (2006.01)
(52) U.S. Cl. ...................... 600/344; 600/310
(58) Field of Classification Search ............ 600/310, 600/322, 323, 340, 344; 602/46, 60, 61, 602/62, 63, 64, 65, 66
See application file for complete search history.

(56) References Cited

U.S. PATENT DOCUMENTS

| 4,510,938 | A | * | 4/1985 | Jobsis et al. ............... 600/344 |
|---|---|---|---|---|
| 4,825,879 | A | | 5/1989 | Tan et al. |
| 4,982,744 | A | | 1/1991 | Stanec |
| 5,090,410 | A | | 2/1992 | Saper et al. |
| 5,437,275 | A | | 8/1995 | Amundsen et al. |
| 5,545,129 | A | * | 8/1996 | Snook .......................... 602/66 |
| 5,800,349 | A | | 9/1998 | Isaacson et al. ............ 600/323 |
| 5,817,010 | A | | 10/1998 | Hibl |
| RE360,000 | | | 12/1998 | Swedlow et al. |
| 5,904,654 | A | | 5/1999 | Wohltmann et al. ......... 600/481 |
| 5,913,819 | A | | 6/1999 | Taylor et al. ............... 600/323 |
| 5,919,133 | A | | 7/1999 | Taylor et al. |
| 5,991,648 | A | | 11/1999 | Levin .......................... 600/344 |
| 6,047,201 | A | | 4/2000 | Jackson, III ................ 600/344 |
| 6,061,584 | A | | 5/2000 | Lovejoy et al. ............ 600/344 |
| 6,256,523 | B1 | | 7/2001 | Diab et al. |
| 6,606,512 | B2 | * | 8/2003 | Muz et al. ................... 600/344 |
| 6,920,345 | B2 | * | 7/2005 | Al-Ali et al. ............... 600/344 |

\* cited by examiner

*Primary Examiner*—Eric F. Winakur
(74) *Attorney, Agent, or Firm*—Marsh Fischmann & Breyfogle LLP

(57) ABSTRACT

The present invention is directed to a holder for use in positioning a pulse oximeter sensor in multiple selectable locations relative to a patient's extremities. The holder includes at least one flexible elongate member that is conformable to and, preferably, about a patient's extremity. A connector on the elongate member is utilized to secure the elongate member to the patient's extremity. Additionally, the elongate member's inside surface contains one or more recesses for selectively receiving a sensor and holding that sensor relative to one or more positions on the inside surface of the flexible sensor holder. The inclusion of multiple recesses allows medical personnel flexibility in positioning a medical sensor. In one embodiment, the holder includes two elongate members for conforming about two portions of a patient's extremity to reduce movement between the extremity and a sensor held by the sensor holder.

61 Claims, 8 Drawing Sheets

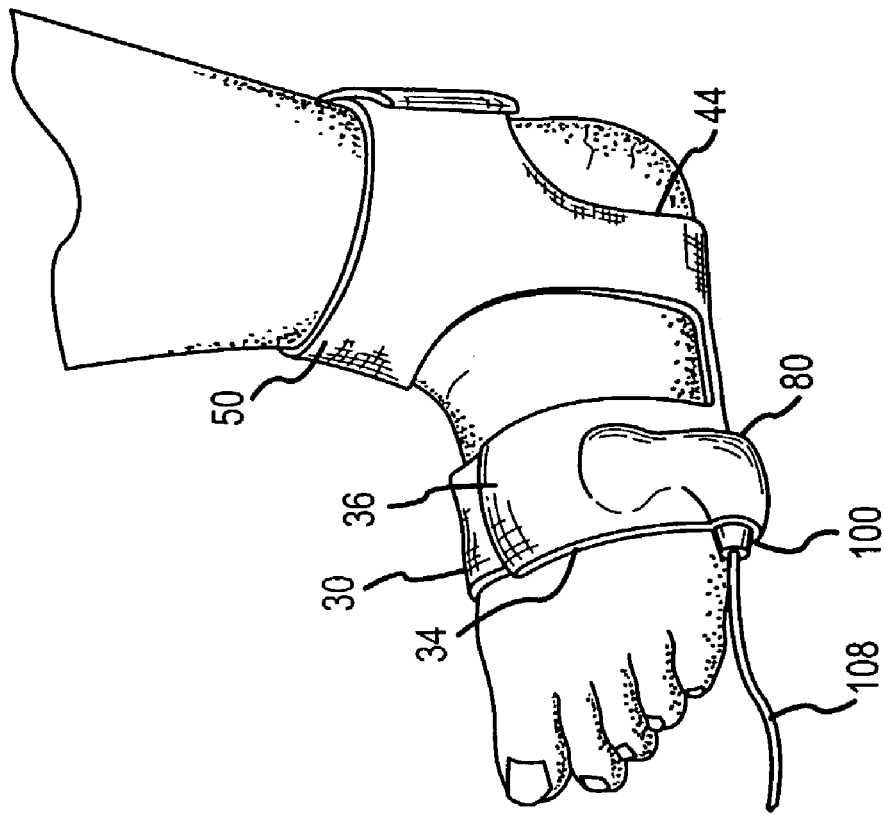
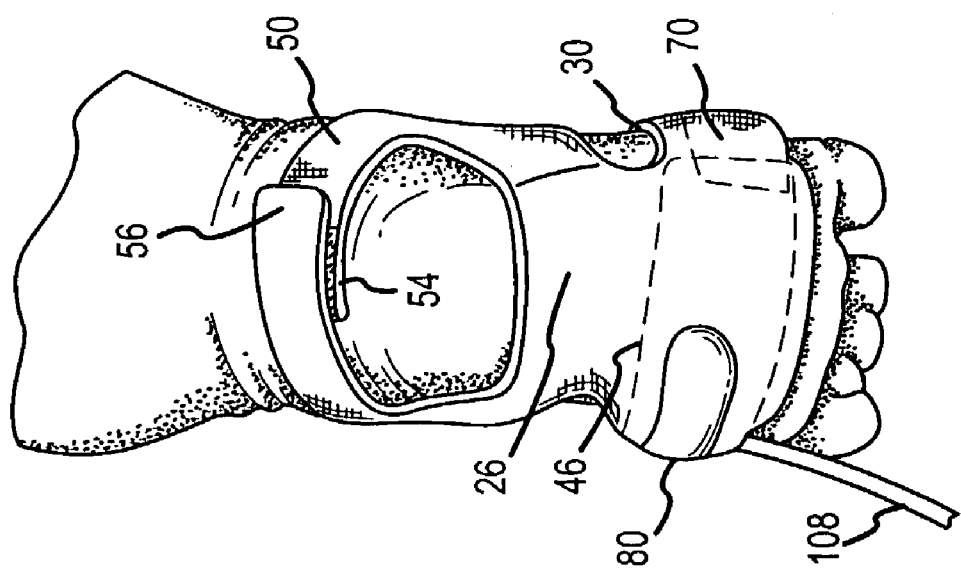

NEONATAL BOOTIE WRAP

CROSS REFERENCE TO RELATED APPLICATIONS

This application claims priority under 35 U.S.C. 119(e)(1) to U.S. Provisional Application No. 60/366,330 entitled: "Neonatal Bootie Wrap," filed on Mar. 21, 2002; the contents of which are incorporated herein as if set forth in full.

FIELD OF THE INVENTION

The present invention is generally directed to a holder for positioning medical sensors relative to a patient's tissue. More specifically, the present invention is directed to a holder for use in positioning a pulse oximeter sensor in multiple selectable locations relative to a patient's extremities.

BACKGROUND OF THE INVENTION

In many medical applications it is desirable to hold one or more sensors in contact with a patient's tissue such that various non-invasive measurements of physiological events may be made. For example, pulse oximeter sensors may be held in contact with a patient's tissue to non-invasively determine pulse rate and/or blood oxygenation levels. When using a pulse oximetry sensor, it is important to properly position the sensor relative to the patient's tissue to ensure its proper operation. If the sensor is held too loosely relative to the tissue, it may not function; in contrast, if the sensor is pressed into the tissue, it may interfere with the physiological properties it is supposed to monitor.

Pulse oximeter sensors generally comprise a detector and at least one light source, which may be focused on or through a patient's tissue. Reflective type pulse oximeter sensors generally focus the light source(s) on the patient's tissue and the detector 'receives' light reflected back. Accordingly, reflective type sensors' light source(s) and detector(s) may be contained in a single discrete unit and be held in contact with the same surface on a patient's tissue. Transmittance type pulse oximeter sensors, which transmit light through tissue a patient's tissue, require that the light source(s) and detector(s) be held to a patient's tissue such that an optical path through the tissue exists between the light source(s) and the detector(s) (e.g., through a finger, ear lobe, hand, foot etc.). Therefore, transmittance type sensors generally have light source(s) and detector(s) that are somewhat separated. Irrespective of the type of pulse oximetry sensor utilized, it is important that a holder provide flexibility in positioning the sensor in order to provide good conformance between the light source(s), detector(s), and the patient's tissue.

There are a number of additional considerations for sensor holders. First, the sensors used with such holders should have the ability to achieve a reliable interface between the sensor and the patient's tissue. Inherent in this first design consideration is the need to securely hold a sensor in place relative to the patient's tissue so the holder and sensor are resistant to unintended removal and/or slippage relative to the tissue. This is especially important for patients that are unable to control their movements or are likely to interfere with the sensor, such as infants. Second, the holder and sensor should be adapted for ready application and removal from the patient with minimal patient discomfort and ease of use for the applicator. Finally, the holder and sensor should provide a gentle interface with the patient's skin.

SUMMARY OF THE INVENTION

It is an objective of the present invention to provide a flexible sensor holder that provides a gentle interface for holding a sensor relative to multiple regions on one or more patient extremities.

Another object of the present invention is to provide a flexible sensor holder that provides improved sensor to tissue interface through the reduction of motion artifact.

Another object of the present invention is to provide a flexible sensor holder that is resistant to accidental removal and/or slippage relative to a patient extremity.

A further objective of the present invention is to achieve one or more of the above objectives where the flexible sensor holder comprises a low part count assembly that is simple to manufacture and cost efficient.

These and other objectives are addressed by the flexible sensor holder of the present invention that is used to hold a medical sensor relative to patient tissue. In a principal application the sensor holder is utilized to hold pulse oximetry sensors, therefore, the term "sensor" hereafter is meant to include both reflective and transmittance type pulse oximetry sensors unless otherwise stated. The flexible sensor holder is conformable to a patient's extremity and contains at least one connector to connect the flexible sensor holder to that extremity. Preferably, the connector is operative to selectively connect a first portion of the flexible sensor holder to a selectable second portion of the flexible sensor holder, thereby allowing the flexible sensor holder to accommodate extremities of varying sizes. A surface of the flexible sensor holder, which interfaces with a patient's tissue upon application to an extremity, includes one or more recesses for selectively receiving a medical sensor. Upon application of the sensor holder to a patient extremity, a sensor disposed within one such recess may be securely held in contact with the patient's tissue without pressing the sensor into the patient's tissue, which may result in, for example, blood vessel constriction (i.e., pressure necrosis).

According to a first aspect of the invention, a flexible sensor holder is provided having a plurality of sensor recesses to allow for added flexibility in positioning a medical sensor relative to a patient extremity. The flexible sensor holder includes a flexible elongate member that is conformable to and, preferably, about a patient's extremity. A connector on the elongate member is utilized to secure the elongate member to the patient's extremity. Additionally, an inside surface of the elongate member contains first and second spaced recesses for selectively receiving a sensor and holding that sensor relative to first and second positions on the inside surface of the flexible sensor holder. The inclusion of the first and second recesses allows medical personnel flexibility in positioning a medical sensor by providing two alternate positions along the elongate member to hold a sensor. Accordingly, upon application of the flexible sensor holder to a patient's extremity, a sensor may be held in first and second alternate positions relative to the patient's tissue.

In one recess spacing embodiment, the first and second recesses are entirely separated and, thereby, capable of holding a sensor to separate positions on the inside surface of the elongate member. These separate recesses may each further comprise discrete portions. For example, each recess may comprise a first portion for receiving a first portion of a sensor and a second portion for receiving a second portion of that sensor. In this regard, a first portion of each recess may be oriented along a portion of the elongate member's length while a second portion of each recess is oriented across the elongate member's width. These first and second recess portions may be connected forming, for example, L-shaped or T-shaped recess configurations. If the discrete portions of each recess are not connected, apertures through the elongate member may be utilized to "weave" a sensor through the elongate member thereby allowing a portion of that sensor to be seated in each recess portion, as will be more fully discussed herein.

Regardless if individual portions of each recess are connected, at least one portion of each recess will preferably extend to a lateral edge of the elongate member to provide access beneath the elongate member when the flexible sensor holder is connected about a patient's extremity. As will be appreciated, this allows for wiring attached to a sensor (e.g., a sensor cable) to pass beneath the flexible sensor holder without applying pressure to the patient's tissue. Further, each recess may extend to different lateral edges of the elongate member, allowing a sensor cable to be routed forward or rearward relative to the elongate member, depending on the recess utilized to receive the sensor. As will be appreciated, in some instances (e.g., patient's with sensitive skin) it may be desirable to route the sensor cable away from the patient to prevent skin irritation and/or to prevent a patient from pulling on the sensor cable.

The recesses may be sized and shaped to receive correspondingly configured sensors (e.g., L-shaped recesses for receiving L-shaped sensors). In this regard, each sensor recess may generally correspond to the shape of a sensor intended for use with the sensor holder. In one embodiment, the first and second sensor recesses are commonly shaped for holding a commonly shaped sensor at alternate locations along the elongate member. However, it will be appreciated that the recesses need not be commonly shaped nor correspondingly-shaped to a medical sensor. For example, the recesses may be differently shaped for receiving different sensors. Furthermore, where differently shaped recess are utilized, one recess may define a shape encompasses the shape defined by the other recess. In this regard, the former recess may be configured to hold the sensors that are utilized with the latter recess while also being configured to receive and hold alternatively shaped medical sensors. In any case, the recesses will preferably have a depth that allows a sensor received therein to be substantially planar with the surface of the elongate member (e.g., the recess depth and sensor thickness are substantially equal). In this regard, upon application to a patient's extremity, pressure applied by the sensor to the patient's tissue may be reduced or eliminated.

Generally, a connector is used to connect the elongate sensor holder around a patient's extremity by connecting a first portion of the elongate member to a second portion of the elongate member. Preferably, the connector is adjustable to allow selective connection of the first portion and second portions such that the length of the elongate member may be adjusted to accommodate extremities of varying sizes. Tapes, snaps and other connectors may be utilized, however, a particularly apt connector comprises of a plurality of loops or hooks attached to a portion of the elongate member's inside surface and a plurality of matching hooks or loops attached to a portion of the elongate member's outside surface. For example, the portion of the elongate member containing hooks/loops on its outside surface may have its inside surface conformed to the patient's tissue, thereby exposing the hooks/loops on its outside surface. The elongate member may then be "wound" around the patient's extremity allowing the matching hooks/loops on the inside surface of the elongate member to connect with the exposed hooks/loops. As will be appreciated, in this embodiment, a first portion of the elongate member will overlap a second portion of the elongate member creating a "flap." In some instances, it may be preferable to orient this flap on the patient to minimize rubbing and/or the patient's ability to disconnect the connector through movement. For example, it may be preferable to orient the flap on the inside of the patient's hand with the flap directed toward the outside edge of the hand.

The use of a sensor holder with multiple recesses extending to opposing sides of the elongate member allows for both selective routing of a sensor cable (i.e., forward or backward) and selective orientation of the flap on the patient's extremity to minimize patient interference and/or discomfort. That is, by utilizing an elongate sensor holder having first and second recesses extending to opposing edges of the elongate member, enhanced patient comfort may be realized. Further, use of multiple recesses may allow for improved sensor placement that may result in improved optical paths through a patient's tissue (e.g., thinner tissue portions) as well as the ability to apply a sensor holder to an extremity without regard to right left extremity orientation.

The recesses may also contain retention means for selectively attaching a sensor to the flexible sensor holder. In this regard, the bottoms of the recesses may be coated with an adhesive and/or a peel-away release liner for selectively adhering a sensor within one of the recesses. That is, the peel-away release liner may be removed to expose an adhesive layer in one of the recesses that is utilized to adhere a sensor therein. Alternatively, a lip may be formed around an inside edge of each sensor recess allowing a sensor having a width greater than a corresponding width of the recess to be seated beneath the lip. This enables a portion of a sensor to be trapped beneath the lip while another part of the sensor has access to the patient's tissue.

In one embodiment the retention means comprises one or more apertures or "slits" passing through the flexible sensor holder. These slits allow a sensor to be weaved through the sensor holder. Preferably, these slits will pass through the sensor holder to allow access to one or more of the recesses. Utilizing one of these slits, a first portion of a sensor may be seated within a recess while a second portion of the sensor extends through the backside of the flexible sensor holder. More preferably, two slits are utilized, allowing the sensor to be threaded through the two slits wherein first and second portions of the sensor are seated in first and second recess portions. As will be appreciated, in this configuration the sensor is weaved through the flexible sensor holder similar to a needle threaded through fabric.

In a second aspect of the present invention, a method for positioning a sensor relative to a patient's tissue is provided. The method includes the steps of positioning a flexible sensor holder relative to a patient's tissue to, for example, determine the best orientation and/or tissue region for sensor placement. One of two provided sensor-holding recesses associated with a patient interface surface of the flexible holder is selected to hold a sensor. This may further include determining which recess will locate the sensor to a preferred location on the sensor holder and/or hold the sensor relative to a preferred tissue region on the patient. A sensor is located within the selected sensor holding recess. This may further entail, inter alia, orienting a sensor cable though a sensor cable slot interconnecting the selected recess to a lateral edge of the sensor holder and/or adhering the sensor to the selected recess. Once the sensor is properly located on the sensor holder (i.e., within the selected recess), a first portion of the sensor holder is connected to a second portion of the sensor holder to fasten the sensor holder about a patient's extremity. As will be appreciated, once attached to the patient's extremity, the sensor is held relative to the patient's tissue allowing the sensor to monitor one or more physiological events.

In a third aspect of the present invention, a flexible sensor holder operative to connect about two portions of a patient's extremity is provided. By providing a dual connection to the patient's extremity, the holder provides for further reduced movement between the sensor and the patient's tissue (e.g., reduced motion artifact). The dual connection flexible sensor holder comprises first and second elongate members that are connected by an interconnecting member. Each of these first and second elongate members is conformable to, and connectable about a patient's extremity. Accordingly, each elongate member contains a connector for selectively connecting that elongate member about the patient's extremity. Finally, the inside surface of at least one of the first and second elongate members contains one or more recesses for selectively receiving a sensor. Preferably, this elongate member will contain at least two recesses to provide medical technicians added flexibility in positioning a sensor relative the sensor holder in accordance with the present invention.

The first and second elongate members are spaced relative to one another so that they may be connected about first and second portions of a patient's extremity. Further, the interconnecting member may also be flexible to allow the first and second elongate members to move relative to one another and, thus, connect about first and second portions of an extremity in transverse planes. For example, the sensor holder may be manipulated such that the first elongate member is connectable around a patient's forefoot and the second elongate member is connectable around the patient's ankle. As will be appreciated, by connecting the flexible holder about two portions of a patient's extremity, the flexible sensor holder is more resistant to accidental slippage and/or removal. Additionally, by connecting about two portions of an extremity in transverse planes, motion between a sensor and a patient's tissue may be reduced.

As noted, at least one of the first and second elongate members contains a first and preferably a second sensor holding recess. Accordingly, if two recesses are utilized, the two recesses may be spaced to allow positioning a sensor in first and second alternate positions relative to the elongate member and/or to first and second alternate tissue regions upon application of the holder to a patient's extremity. For example, upon application of the flexible sensor holder a patient's foot and ankle, a first sensor recess may be available to hold a sensor to the inside edge of the patient's foot and a second sensor recess may be available to hold a sensor to the outside edge of the patient's foot. As will be appreciated, when using a transmittance type pulse oximetry sensor it is generally desirable to have an optical path through a thinner portion of a patient's tissue (e.g., an outside edge of a patient's foot); therefore, flexibility in placing a sensor on the sensor holder may provide an improved optical path and, therefore, improved sensor performance. Further, by providing flexibility in placing the sensor on the sensor holder, the sensor holder may be applied to right or left extremities.

In accordance with a fourth aspect of the present invention, a method of providing dual point connection for positioning a sensor relative to a patient's tissue is provided. In this regard, a flexible sensor holder operative to be connected about two portions of a patient's extremity is provided. The flexible sensor holder is positioned relative to the patient's extremity where sensor placement is desired. A sensor is located on the patient interface surface of the flexible sensor holder (e.g., received/adhered in a selected sensor holding recess). Once the sensor is located and the flexible holder is properly positioned, a first portion of the flexible holder is connected about a first portion of a patient's extremity and then a second portion of the flexible holder is connected about a second portion of the patient's extremity. As will be appreciated, the first and second connecting steps secure the sensor holder to the patient's extremity, which in turn holds the sensor relative to a patient's tissue. The first and second connecting steps may be performed on any appropriate patient extremity, however in a preferred application they are connected about transverse planes of a patient's extremity, such as a foot and ankle, to provide increased isolation between the patient's tissue and the sensor.

In a fifth aspect of the present invention, a flexible sensor holder is provided that is convertible from a dual connection flexible sensor holder to a single connection flexible sensor holder. In this regard, the flexible sensor holder comprises first and second elongate members that are each conformable to, and connectable about a patient's extremity. An interconnecting member connects the first elongate member to the second elongate member. One or both of the interfaces between the interconnecting member and the first and second elongate members is selectively detachable. That is, one or both of the elongate members are releaseably attached to the interconnecting member.

The releasable attachment of the interconnecting member allows one or both of the elongate members to be disconnected from the interconnecting member, thus, converting the dual connection sensor holder into a single connection sensor holder. The interconnecting member may be releaseably attached to either or both the first or second elongate members in any manner that is readily detachable by a medical technician. Preferably, at least one of the interfaces between the interconnecting member and the elongate members will be perforated to allow one or both of the elongate members to be disconnected by hand.

The disconnected elongate member may include a connector for connecting about a patient's extremity and may contain one or more recesses for holding a sensor relative to a patient's tissue. As will be appreciated, this allows the disconnected elongate member to be used as a single connection sensor holder for holding a sensor relative to a patient's tissue. As will be further appreciated, the present aspect of the invention allows a medical facility to stock a single flexible sensor holder that may be used in a variety of contexts. That is, the present aspect allows a technician to convert a dual connection sensor holder into a single connection sensor holder when needed, thus, providing additional flexibility in sensor application.

In a further aspect of the present invention, a flexible sensor holder comprising releaseably laminated layers is provided. As presented, the flexible sensor holder generally comprises a compressible material layer, in which one or more recesses may be formed, a backing layer releaseably laminated to the compressible material layer to impart structural qualities, and a connector to hold at least a first portion of the flexible sensor holder to a second portion of the flexible holder once wrapped about a patient's extremity.

The compressible material layer may be formed from foam, neoprene, rubber, fabric, composites thereof and other suitable materials that permit desired compression. Additionally, the compressible material will typically be of a thickness that allows one or more recesses of a predetermined depth to be formed therein. To facilitate manufacture, a preferred embodiment utilizes a compressible material having the same thickness as the desired recess depth. In this regard, the recesses may be formed by "punching" holes entirely through the compressible material layer and then laminating this layer to a backing layer.

The backing layer may be any flexible material and will preferably have a increased tensile strength in relation to the compressible material layer. In addition, for pulse oximetry applications it is preferable that the backing material provide light blocking characteristics to reduce noise effects of ambient light. In any case, the backing layer is releaseably laminated to the compressible material layer. In a preferred embodiment, the backing layer comprises a hook and loop material. This hook and loop material may have a plurality of hooks on a first side and a plurality of loops on a second side. Accordingly, the compressible material layer may contain two or more layers, e.g., a compressible material for interfacing with a patient's tissue and a hook or loop attachment layer interconnected to one side of the compressible material. This attachment layer may be releaseably laminated with the hook/loop backing material. Alternatively, a surface of the backing layer (e.g., a plurality of hooks) may be laminated directly to the compressible material layer (e.g., an open cell foam).

By extending the releaseably laminated backing layer beyond at least one end of the compressible material layer (s), one side of the backing material (e.g., hooks) may connect to the other side (e.g., loops) when the flexible sensor assembly is wrapped around an extremity, providing sensor holder that does not require a separately formed connector. The use of a compressible material and backing layer releaseably laminated together provides another benefit, namely, individual adjustment of the flexible sensor holder. For example, if an elongate flexible sensor holder was too long, the backing layer and compressible material may be separated, cut to a desired length, re-laminated, and applied to a patient's extremity. Unlike other configurations, this embodiment allows altering the sensor holders length without affecting the holder's connector mechanism.

BRIEF DESCRIPTION OF THE DRAWINGS

FIGS. 3a and 3b show front and rear perspective views of the flexible sensor holder of FIG. 1 applied to a patient's foot and ankle;

DETAILED DESCRIPTION

The present invention will now be described in relation to the accompanying drawings, which at least assist in illustrating its various pertinent features. The present invention, a flexible sensor holder, is described in all embodiments in conjunction with a transmittance type pulse oximetry sensor; however, it is to be expressly understood that the flexible sensor holder of the present invention may be utilized with reflective type pulse oximetry sensors as well as other non-invasive medical sensors.

Figure 1:
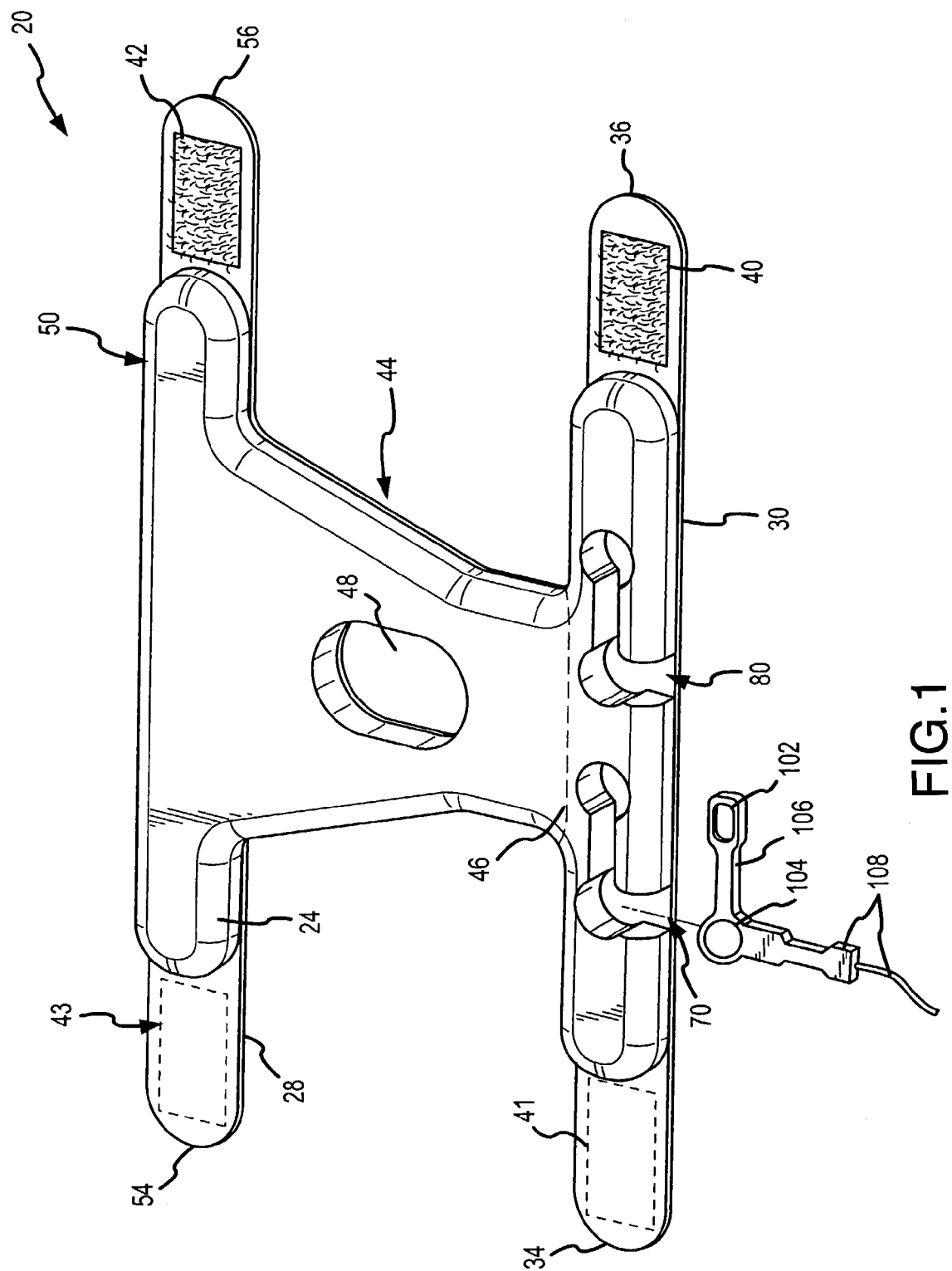
FIG. 1 shows a perspective view of a two elongate member flexible sensor holder for use with an L-shaped pulse oximetry sensor.

FIG. 1 shows a first embodiment a dual connection flexible sensor holder 20. The dual connection flexible holder 20 includes a first elongate member 30 for conformably wrapping around a first portion of a patient's extremity, a second elongate member 50 for conformably wrapping around a second portion of a patient's extremity and an interconnecting member 44 interconnecting the first and second elongate members 30, 50. The interconnecting member 44 attaches the two substantially parallel elongate members 30, 50 such that the flexible sensor holder 20 generally comprises an H-shape prior to application to a patient's extremity.

The flexible sensor holder 20 further contains a compressible material layer 24 and a backing layer 28. The compressible material layer 24 makes up part of or all of the inside surfaces for the first and second elongate members 30, 50 and the interconnecting member 44 while the backing layer 28 makes up the sensor holder's outside surface. As shown, the compressible material layer 24 does not extend to the ends of the first and second elongate members 30, 50, however, it will be appreciated that in alternative embodiments the compressible material layer may fully cover the inside surface of the elongate members 30, 50. The compressible material layer 24 provides for a gentle patient interface while the backing layer 28 provides light blocking qualities and structural integrity for the dual connection sensor holder 20.

Formed into the compressible material layer 24 on the first elongate member 30 are first and second recesses 70 and 80. These recesses 70, 80 are used to selectively receive a sensor 100 and hold that sensor 100 relative to a patients tissue upon application of the flexible sensor holder 20 to a patient's extremity. As shown, the sensor 100 is an L-shaped transmittance type pulse oximetry sensor that contains an emitter 104 and detector 102 interconnected by a flexible wiring conduit 106 and a cable 108 interconnecting the sensor 100 to a pulse oximetry monitor (not shown).

The flexible sensor holder's first and second elongate members 30, 50 each contain a hook and loop connector for connecting the first and second elongate members 30, 50 about a patient's extremity. The connectors comprise a plurality of hooks 40, 42 located on the inside surface of a first portion 36, 56 of each elongate member 30, 50 and a corresponding plurality of loops 41, 43 (shown in phantom) are located along a portion of the length of the outside surface 7 of each elongate member. The loops 41, 43 located on the elongate member's outside surfaces may be formed as a strip aligned with that member's longitudinal axis, thus providing means for adjusting each elongate member 30, 50 to fit about extremities of varying sizes. Though described as a hook and loop connector, it will be appreciated that any appropriate connector means (e.g., tapes, snaps, etc.) may be utilized.

The two elongate members 30, 50 may be connected around two portions of a patient's extremity thereby providing a dual connection sensor holder 20 that provides increased sensor holding force. As will be appreciated, by increasing the holding force, motion between the sensor 100 and the tissue may be reduced and, thus, provide for enhanced sensor readings. Alternatively, the force exerted by each elongate member 30, 50 may be reduced in comparison to a flexible sensor holder utilizing a single elongate member while still adequately securing the sensor 100 to the patient's tissue. This is especially desirable in cases where the patient has sensitive skin, such as premature infants. Additionally, tightly wrapping the sensor holder may affect blood flow within the tissue and, therefore, distort sensor readings.

The dual connection flexible sensor holder 20 may be utilized to secure a sensor 100 to any patient extremity. However, the configuration of the dual connection flexible sensor holder 20 of the present embodiment is especially apt for holding a sensor 100 on a patient's foot and leg/ankle. To facilitate conformance to the foot/ankle, the interconnecting member 44 contains an aperture 48 that is located and sized to receive a patient's heel upon application of the dual connection sensor holder 20 to the patient's foot and ankle (See FIGS. 3*a* and 3*b*). In this regard, the first elongate member 30 and second elongate member 50 are conformably wrapped and secured around the patient's forefoot and the ankle, respectively.

In order to apply the sensor holder to the patient's foot, the ends 34, 54 of each elongate member 30, 50 which do not contain hooks on their inside surfaces are conformed about the patient's foot/ankle such that the plurality of loops 41, 43 on their outside surface are exposed. Then, the end 36, 56 of each elongate member 30, 50 containing a plurality of hooks 40, 42 on their inside surface, are pulled over the corresponding loops 41, 43, securely attaching each elongate member 30, 50 about the extremity. This arrangement creates a sensor holding "bootie" or "sandal" wrap on the patient's foot and ankle where the first and second elongate members 30, 50 securely fasten about the patient's ankle and foot in two transverse planes. When utilized with a patient's foot and ankle, the dual connection flexible sensor holder 20 provides enhanced resistance to accidental removal and/or slippage. As will be appreciated, this is particularly important in neonatal and infant applications, as these patients are unable to control their movements and therefore apt to dislodging sensors.

As shown in phantom lines in FIGS. 3*a* and 3*b*, when applied to a patient's foot, the first and second sensor recesses 70, 80 are located on the inside and outside edge of the foot, providing a medical technician flexibility in sensor placement. As will be appreciated, it is generally desirable to utilize the thinnest part of the foot (e.g., the outside edge) to obtain better optical communications between the emitter 104 and detector 102 when using a transmittance type pulse oximetry sensor 100. As shown in FIG. 3B, the sensor 100 is held by the second recess 80 on the thinner outside edge of the patient's foot. By providing a sensor holder 20 with two spaced recesses 70, 80, the sensor holder 20 can hold a sensor 100 relative to the inside or outside edge of a patient's foot regardless of which foot the holder 20 is applied, providing a bootie holder that is non right/left extremity specific.

Figure 2:
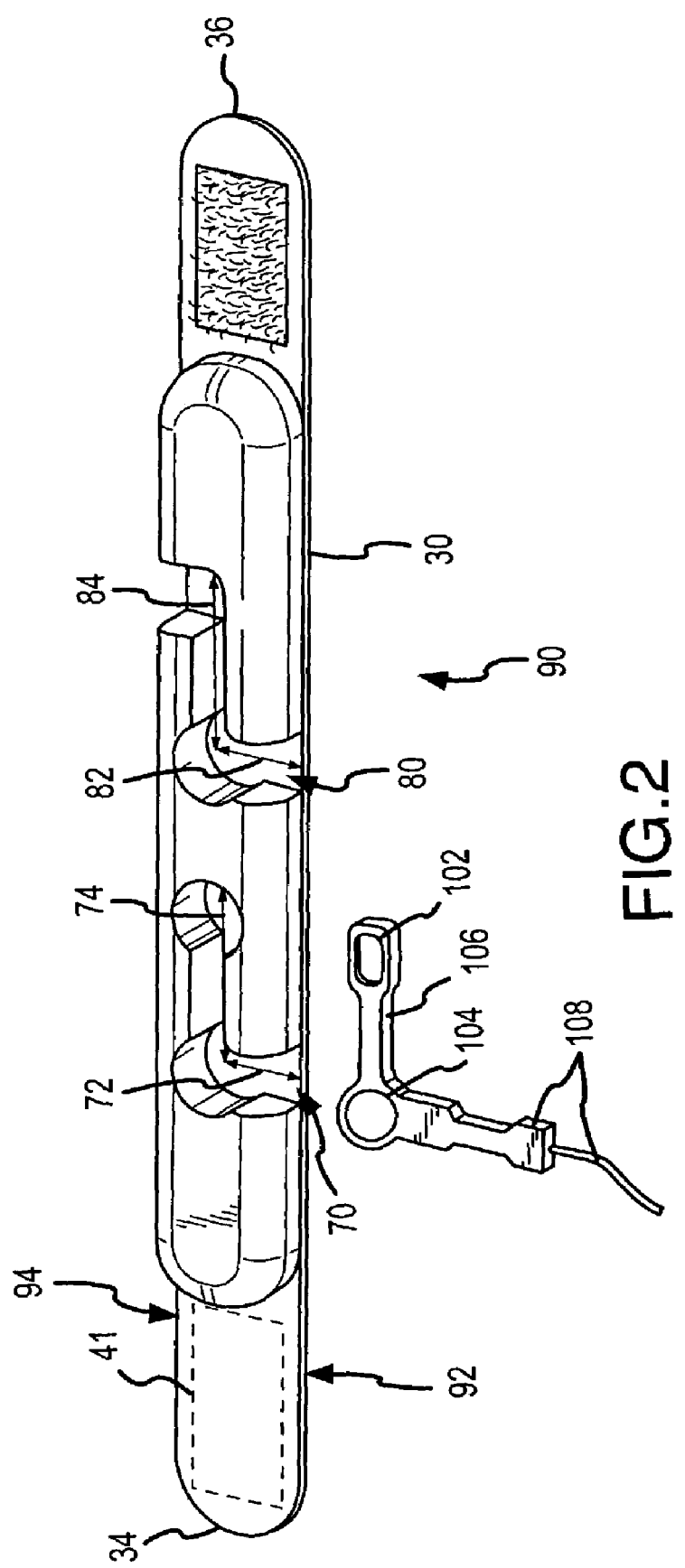
FIG. 2 shows a perspective view of a single elongate member flexible sensor holder for use with an L-shaped pulse oximetry sensor.
Figure 4:
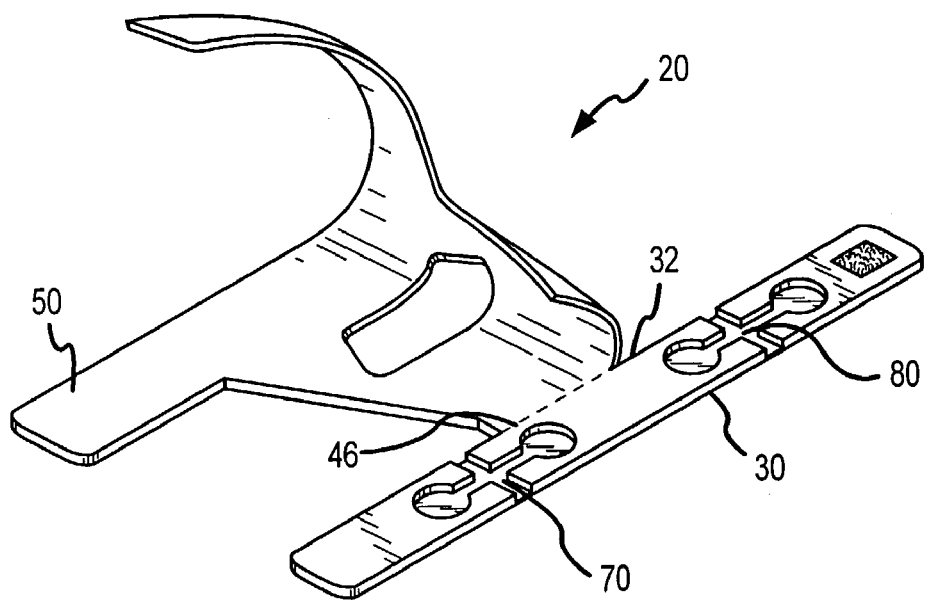
FIG. 4 shows a perspective view the two elongate member flexible sensor holder of FIG. 1 being converted to the single elongate member flexible sensor holder of FIG. 2.
Figure 5:
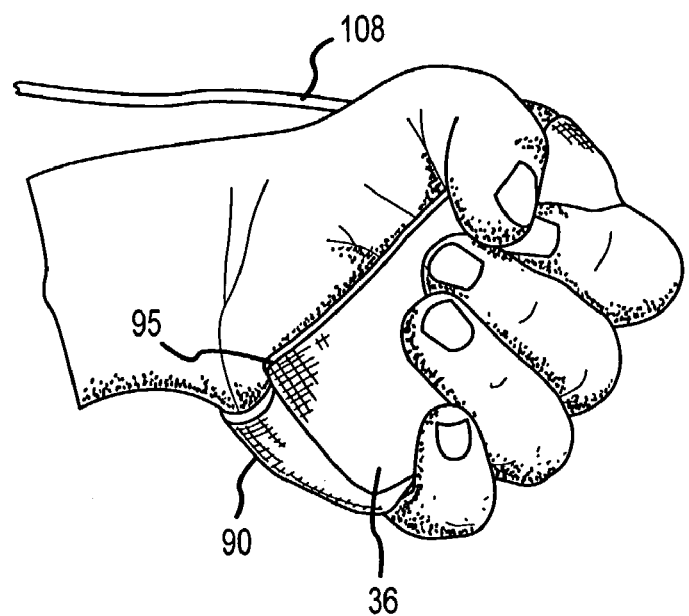
FIG. 5 shows the flexible sensor holder FIGS. 2 and 4 applied to a patient's hand.

Referring to FIGS. 1, 2, 4 and 5, there is shown the selective removal of the first elongate member 30 from the dual connection sensor holder 20, effectively converting the dual connection sensor holder 20 or "bootie" wrap of the first embodiment (FIG. 1) to a single connection sensor holder 90 shown in FIGS. 2 and 5. In this regard, the bootie wrap's first elongate member 30, which contains the first and second recesses 70, 80, is releaseably attached to the interconnecting member 44. As shown in FIGS. 1 and 4, the interface between the interconnecting member 44 and the first elongate member 30 contains a plurality of perforations 46. These perforations 46 extend through the flexible sensor holder 20 from the inside surface through the outside surface, enabling a medical technician to "tear" the first elongate member 30 away from the interconnecting member 44 when a single connection sensor holder 90 is desired. As shown in FIG. 2, this leaves a single connection sensor holder 90 having one elongate member 30 containing first and second recesses 70, 80, and a hook and loop connector 40, 41 for connecting the elongate member 30 about a patient's extremity. This single connection sensor holder 90 as shown in FIG. 2 may be used to hold a sensor 100 to a patient's hand as shown in FIG. 5, or any other extremity, such as a forearm, ankle, etc. Though shown as a removable portion of the dual connection sensor holder 20, it will be appreciated that the single connection sensor holder 90 may be separately produced.

The recesses 70, 80 (See FIGS. 1 and 2) are disposed in a spaced relationship in first and second positions on the elongate member 30. As shown in FIGS. 1 and 2 the recesses are entirely separated such that either recess (or possibly both recesses) may be selectively utilized to hold a sensor 100 relative to a first or second position along the elongate member 30. For simplicity, the rest of the discussion regarding the recesses will be directed to the single connection sensor holder 90 of FIG. 2, however, it will be appreciated that the following description is applicable to dual connection sensor holder 20 of FIG. 1. Each recess 70, 80 further comprise a first and second interconnected portions 72, 74 and 82, 84 respectively. The recesses 70, 80 are formed generally in the shape of an "L" to correspond with the L-shaped pulse oximetry sensor 100. In this regard, the first portion 74, 84 of each recess 70, 80 extends along a portion of the length of the elongate member 30, while the second interconnecting portions 72, 82 extend across a portion of the width of the elongate member 90. These second recess portions 72, 82 provide access for the sensor's cable 108 beneath the elongate member 30 when the elongate member is applied to a patient's extremity, as shown in relation to the dual connection sensor holder 20 in FIG. 3*b*.

As will be appreciated, these second or "access" portions 72, 82 of each recess 70, 80 allow a sensor cable 108 to exit the sensor holder 90 without applying pressure to the patient's tissue. Further, these access recess portions 72, 82 may extend to different lateral edges 92, 94 to provide a sensor holder 90 that allows a sensor cable 108 to be selectively routed out of either lateral edge 92, 94 of the sensor holder. As shown in FIGS. 3*a* and 3*b* for the two elongate member sensor holder 20, the sensor cable 108 exits the sensor holder 20 from the front. By utilizing the other recess to hold the sensor 100, the cable 108 could exit toward the heel of the foot. As will be appreciated, in cases where the patient has sensitive tissue (e.g., premature infants) it is generally desirable to direct the cable 108 away from the patient. In contrast, for less sensitive patients it may be desirable to route the sensor cable 108 toward the patient where it may be affixed (e.g. taped) to prevent the cable 108 from pulling on the sensor 100 during patient movement.

In the case of the single connection sensor holder 90, the sensor cable 108 can be routed forward or backward from either recess 70, 80 by turning the holder 90 around such that each recess' access opening is in the desired direction. However, the overlap created by one end of the elongate member 30 being secured over a second end of the elongate member 30 creates a flap that may cause patient irritation or provide means for a patient to dislodge the sensor holder 90. Therefore, it may be desirable to orient this flap in a particular location. As shown in FIGS. 2 and 5 the second end 34 of the elongate member 30 is placed against the palm of the patient's hand and the first end 36 is connected over the second end 34 to secure the single connection sensor holder 90 to the patient's hand. This connection creates a flap 95 where the first end 36 overlaps the second end 34. In order to orient this flap 95 in a desired direction (e.g., in the palm of the hand with the flap end away from the thumb) and route the sensor cable 108 a particular direction (i.e., forward or backward), two sensor recesses 70, 80 with openings to opposite lateral edges of the sensor holder 90 are required.

Figure 6:
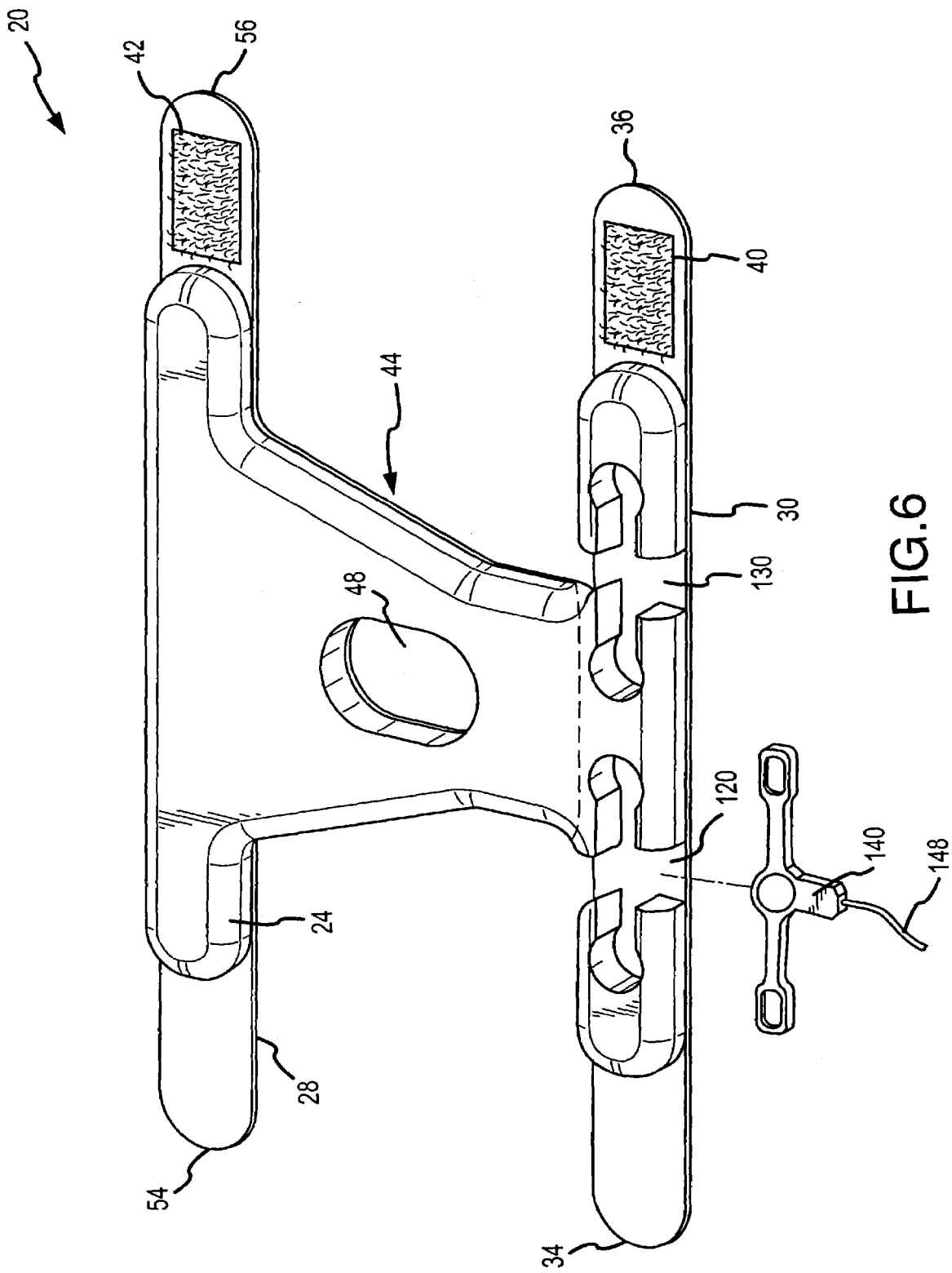
FIG. 6 shows a perspective view of a two elongate member flexible sensor holder for use with a T-shaped pulse oximetry sensor.

FIG. 6 shows an alternate embodiment of the flexible sensor holder of FIG. 1. The sensor holder of FIG. 6 is substantially identical to the sensor holder of FIG. 1 except for the shape of the sensor recesses 120, 130. Accordingly, like features are labeled with like numbers. In this embodiment, the first and second recesses 120, 130 generally define a T-shape wherein a portion of each recess extends from a first lateral edge to a second lateral edge on the elongate member 30 while a second portion extends along the length of the elongate member 30. The T-shaped recesses 120, 130 may be utilized with the T-shaped sensor 140 shown. As will be appreciated, in this embodiment, the T-shaped sensor 140 may be applied to either recess 120, 130 while its cable 148 is routed forward or backwards from either recess 120 130, thus, further facilitating sensor positioning. As with the embodiment shown in FIG. 1, the elongate member 30 having the T-shaped recesses 120, 130 may be selectively removed from the H-shaped flexible sensor holder 20 to provide a single connection sensor holder.

Figure 7A:
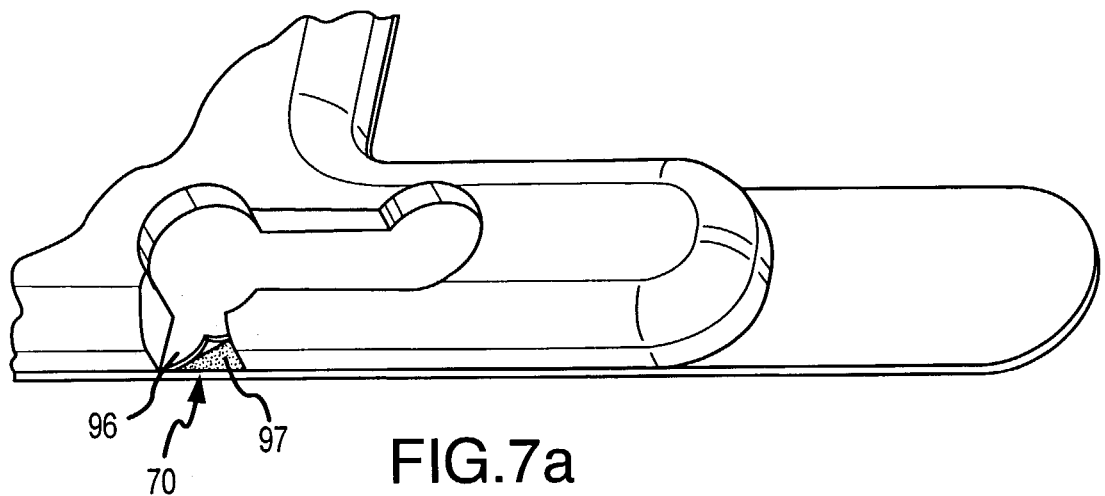
FIGS. 7a, 7b and 7c show alternate retention means for holding a sensor within a recess.
Figure 7B:
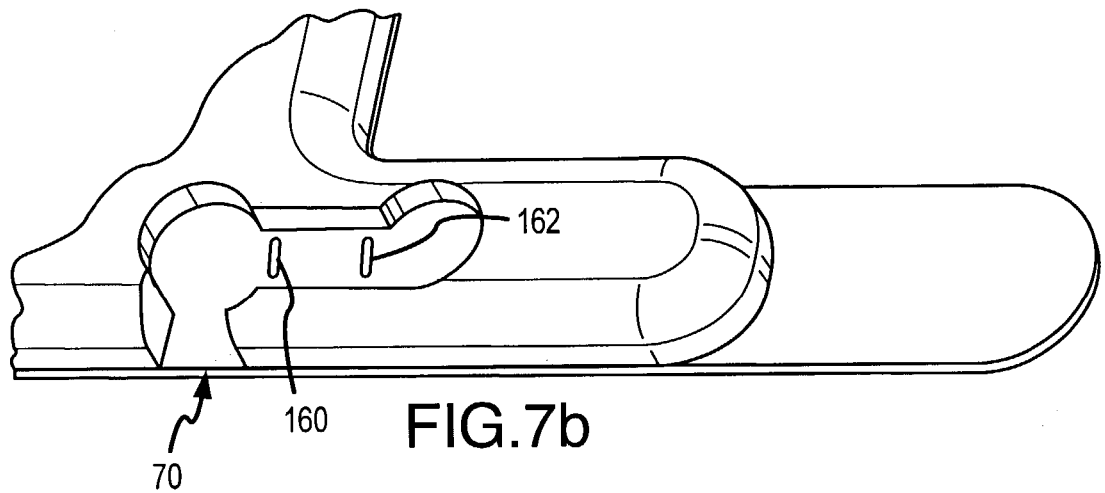
Figure 7C:
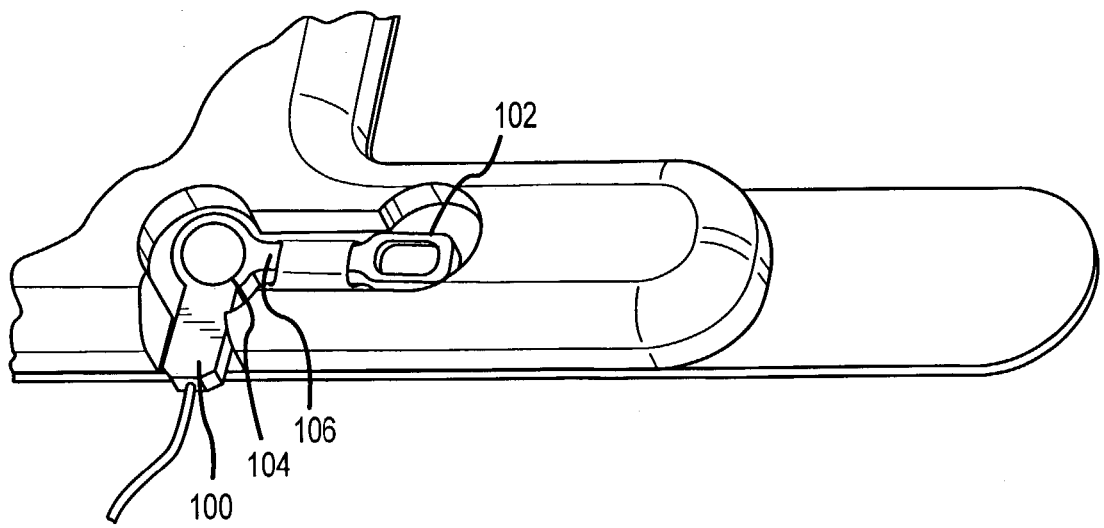

FIGS. 7a, 7b and 7c show alternative means for securing a sensor 100 to the recesses utilized with any of the above described flexible sensor holders. In one embodiment, the bottom of a recess 70 is coated with an adhesive 97 for selectively adhering a sensor 100 within that recess 70. This adhesive 97 is covered by a peel away release sheet 96 that may be removed prior to sensor adhesion. This release sheet 96 prevents the adhesive 97 from contacting and possibly irritating a patient's tissue. FIGS. 7b and 7c show an alternate sensor retention means that utilizes two sensor retention slits 160 and 162 formed in the bottom on an L-shaped sensor recess 70. These retention slits pass through the flexible sensor holder from its inside surface to its outside surface. When utilized with the L-Shaped sensor 100, the sensor is inserted through the first retention slit 160 from the top surface and back through the second retention slit 162 from the sensor holder's bottom surface until the sensor 100 seats within the recess (FIG. 7c). As will be appreciated, once the flexible sensor holder 20 is applied to a patient's tissue, the sensor 100 is securely fastened to the sensor holder without the use of any adhesives.

Figure 8:
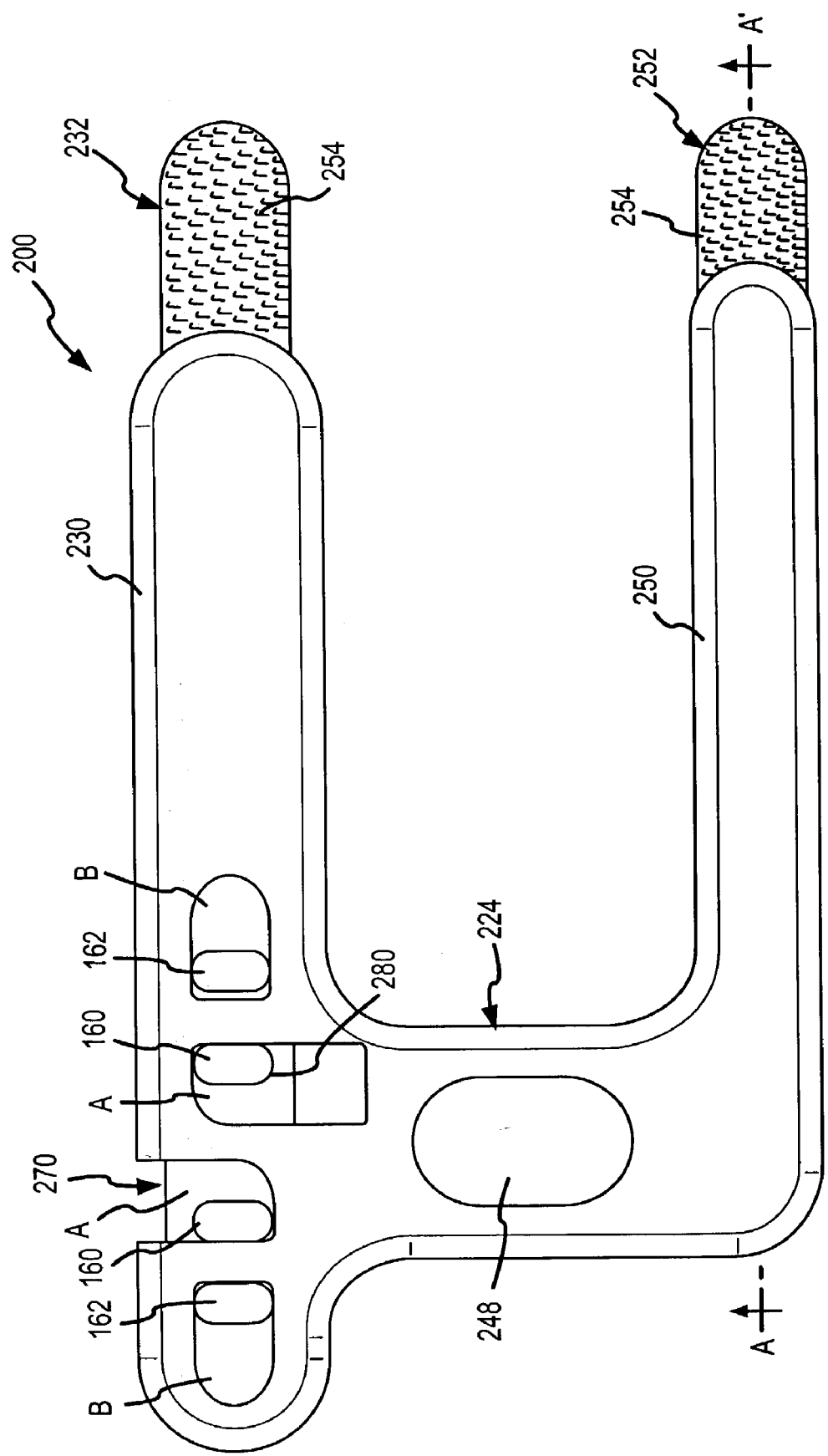
FIG. 8 shows an alternate embodiment of a two elongate member flexible sensor holder that utilizes releaseably laminated layers and sensor retention slits as shown in FIGS. 7b and 7c.

FIG. 8 shows another embodiment of a dual connection sensor holder of the present invention for use with the L-shaped pulse oximetry sensor 100. The flexible holder 200 includes a first elongate member 230 for conformably wrapping around a first portion of a patient's extremity, a second elongate member 250 for conformably wrapping around a second portion of a patient's extremity, and an interconnecting member 240, containing a "heel" aperture 248, that interconnects the first and second elongate members 230, 250. The interconnecting member 240 connects the two substantially parallel elongate members 230, 250 such that the flexible sensor holder 200 generally comprises a U-shape prior to application to a patient's extremity.

The sensor holder 200 contains a compressible material layer 224 that makes up the sensor holder's patient interface surface. This compressible material may be formed from foam, neoprene, rubber, fabric, composites thereof and other suitable materials as long as the compressible material has a plurality of void spaces within its structure to permit compression. In this regard, all that is required is that the compressible materials have a compression setting that, upon application of a predetermined pressure to the material, substantially conforms to the surface contacting the compressible material. The sensor holder 200 also contains two separate backing strips 232 and 252 releaseably interconnected to the outside surface of each elongate member 230 and 250, respectively. As will be appreciated, in this embodiment the interconnecting member 248 contains no backing layer.

Figure 9:
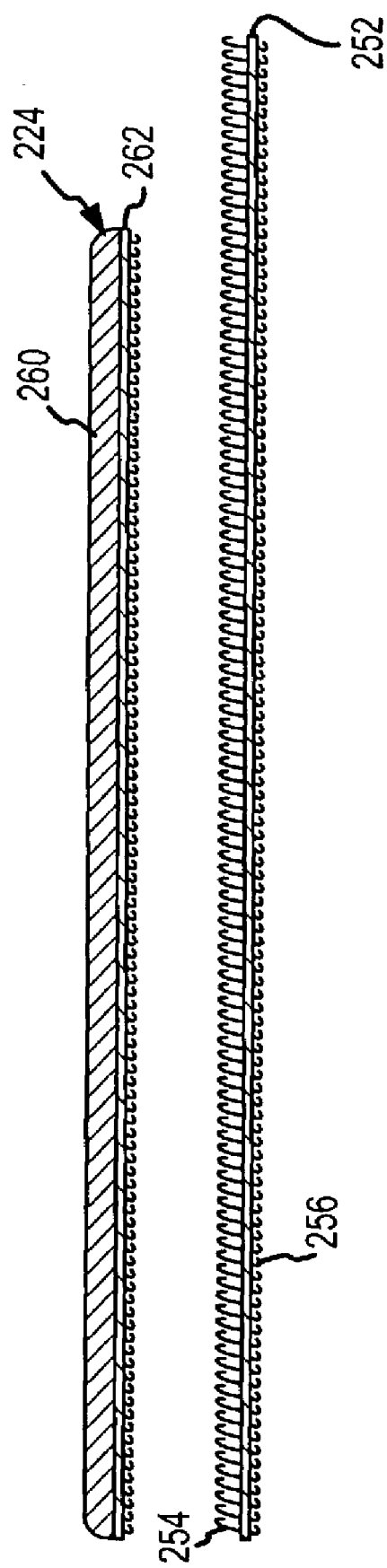
FIG. 9 shows an exploded cross sectional view of a portion of the sensor holder of FIG. 8.

FIG. 9 shows an exploded cross sectional view taken along section lines A–A' of FIG. 8 (not to scale). As shown the backing strip 252 is formed from a hook and loop tape having an inside surface covered by a plurality of hooks 254 and an outside surface covered by a plurality of matching loops 256. The compressible material layer 224 comprises a two-layer structure that contains an open cell foam layer 260 affixed (e.g., glued, sonically welded, etc.) to a layer of loop material 262. Accordingly, when the sensor holder 200 is manufactured, the backing layer hooks 254 are releaseably laminated to the compressible material layer's loop material 262. As will be appreciated, this provides a secure connection between the compressible material layer 224 the backing strip 252 without the use of additional adhesives or processing steps, thereby providing a simplified production process.

Referring to FIG. 9, it will be noted that the backing strips 232, 252 extend beyond the end of the compressible material layer 224 of each elongate member 230, 250. This enables the exposed hooks 254 on each backing strip's inside surface to engage the loops 256 contained along the length of their outside surfaces when the elongate members 230 and 250 are wrapped around a patient's extremity. As will be appreciated, these hooks 254 may engage the loops 256 anywhere along the length of the backing strips 232, 252 providing enhanced adjustability to accommodate extremities of varying sizes. Further, the use of hook and loop tape backing strips 232, 252 eliminates the need for a separate connector reducing the sensor holder's overall part count.

The use of the hooks and loops to releaseably laminate the backing strips 232, 252 to the compressible material 224 provides an additional benefit, namely the ability to adjust (e.g. shorten) the length of each elongate member 230 and 250. That is, by separating the compressible material 224 from the backing strips 232, 252, the compressible material 224 and backing strips 232, 252 may be trimmed to a desired length. That is, the right side of the elongate members 230 and 250 as shown in FIG. 8 may be shortened. After trimmed to their desired length, the elongate members 230 and 250 may be re-laminated and may be applied to a patient's extremity.

Formed into the compressible material layer 224 on the first elongate member 230 are first and second sensor holding recesses 270 and 280. Again, these recesses 270, 280 are used to selectively receive an L-shaped pulse oximetry sensor 100 and hold that sensor 100 relative to a patients tissue upon application of the flexible sensor holder 200 to a patient's extremity. As shown, each sensor holding recess 270, 280 comprises two separated recess portions 'A' and 'B' that are formed by cutting out and removing sections of the compressible material layer 224. A portion 'B' of each recess 270, 280 is shown aligned with along the first elongate member's center line and is sized to receive the emitter portion 104 of the pulse oximetry sensor 100 while the second portion 'A' of each recess 270, 280 is sized to receive the detector portion 102 of the pulse oximetry sensor 100. In this embodiment, the first and second recess portions 'A' and 'B' are separated by a section of compressible material 224 that forms sensor a retaining member 276.

To enable the L-shaped sensor 100 to be inserted into one the recesses 270, 280, the backing strip 232 beneath each recess portion 'A' and 'B' contains sensor retention slits 160, 162. In this regard, the emitter 104 is inserted through the first slit 160 from the topside of the sensor holder 200. The emitter 104 is then routed through the second slit 162 from the backside of the sensor holder 200 until the emitter 104 seats in the second recess. At this point, the sensor's detector 102 is seated in the sensor recess portion 'A' and the emitter 104 is seated within sensor recess portion 'B.' More importantly, the flexible wiring conduit 106 interconnecting the emitter 104 and detector 102 is trapped behind both the backing strip 232 and compressible material layer 224 between the slits 160, 162. As will be appreciated, this "weaved" arrangement securely fastens the sensor 100 within the sensor holder 200 without the need for any adhesives that may contact or otherwise irritate the patient's tissue.

As with the embodiments described above, the U-shaped flexible sensor holder 200 may be utilized to provide a dual point connection on any patient extremity, however, this configuration is again particularly apt for placement on a patient's foot and ankle. In this regard, after a sensor is inserted within one of the sensor holding recesses 270, 280 a patient's foot would be placed on the flexible sensor holder 200 having the heel centered within the interconnecting member's aperture 248 with the patient's toes extending past the sensor holding recesses 270 and 280. The first elongate member 230 would then be wrapped around the patient's forefoot until the hooks on the backing strip's inside surface engage the loops on its outside surface. The second elongate member 250 would then be affixed about the patient's ankle/lower leg. In application, the U-shaped sensor holder 200 is substantially similar to the H-shaped sensor holder shown in FIGS. 3a and 3b.

While various embodiments of the present invention have been described in detail, it is apparent that modifications and adaptations of those embodiments will occur to those skilled in the art. However, it is to be expressly understood that such modifications and adaptations are within the spirit and scope of the present invention, as set forth in the following claims.

The invention claimed is:

1. A flexible holder for positioning a sensor relative to a tissue region on a patient, said holder comprising:
   a flexible elongate member having inside and outside surfaces, said elongate member conformable relative to a patient's extremity;
   a first recess located on said inside surface of said elongate member for selectively receiving a sensor in a first position relative to said elongate member;
   a second recess located on said inside surface of said elongate member for selectively receiving a sensor in a second position relative to said elongate member, wherein said first and second positions are spaced; and
   a connector for connecting said elongate member to said extremity.

2. The flexible holder of claim 1, wherein said first and second recesses are spaced such that each said recess includes at least a first portion that is at least partially separated from the other said recess.

3. The flexible holder of claim 2, wherein said first and second recesses are spaced such that said first and second recesses are separately positioned relative to one another on the inside surface of said elongate member.

4. The flexible holder of claim 3, wherein said first and second recesses are disposed such that said recesses are capable of selectively holding a sensor relative to separate portions of a patient's tissue when said holder is connected to said extremity.

5. The flexible holder of claim 1, wherein said first and second recesses each comprise a different shape.

6. The flexible holder of claim 1, wherein a shape defined by one of said first and second recesses would be fully encompassed by a shape defined by the other of said first and second recesses.

7. The flexible sensor of claim 6, wherein said first and second recesses are commonly shaped.

8. The flexible holder of claim 1, wherein said first and second recesses each further comprise a first portion oriented along a portion of the length of said elongate member and a second portion extending across a portion of the width of said elongate member, wherein said first and second portions interconnect.

9. The flexible holder of claim 8, wherein said each said second portion extends to a lateral edge of said elongate member.

10. The flexible holder of claim 9, wherein each said second portion extends to a different lateral edge of said elongate member.

11. The flexible holder of claim 9, wherein said first and second portions of each said recess define an L-shaped configuration.

12. The flexible holder of claim 11, wherein said first and second recesses are adapted to matingly receive a correspondingly-shaped sensor.

13. The flexible holder of claim 9, wherein each said second portion extends across the width of said elongate member from a first lateral edge to a second lateral edge.

14. The flexible holder of claim 1, wherein said first and second recesses are sized to receive a sensor such that an inside surface of said holder and a top surface of said sensor are substantially planer.

15. The flexible holder of claim 1, wherein said first and second recesses further comprise retention means for selectively attaching a sensor to said holder.

16. The flexible holder of claim 15, wherein said retention means comprises an adhesive coating on the bottom of each said recess.

17. The flexible holder of claim 16, wherein said adhesive coating is covered with a removable release sheet that may be selectively removed prior to receiving said sensor.

18. The flexible holder of claim 15, wherein said retention means comprises a lip formed around the inside edge of at least part of each said recess.

19. The flexible holder of claim 1, wherein said connector is an adjustable connector for selectively connecting a first portion of said elongate member to a selectable second portion of said elongate member such that said holder is securely connectable around said extremity.

20. The flexible holder of claim 19, wherein said connector comprises a plurality of hooks attached to said first portion of said elongate member and a plurality of matching loops attached to said second selectable portion of said elongate member.

21. A method for positioning a sensor relative to a tissue region on a patient, said method comprising the steps:
  positioning a flexible sensor holder relative to a patient's tissue;
  selecting one of two provided sensor holding recesses on a patient interface surface of said flexible sensor holder, wherein said sensor holding recesses are operative to hold a sensor relative to first and second positions on said flexible holder;
  locating a sensor in said selected sensor holding recess;
  interconnecting a first portion of said flexible sensor holder to a second portion of said flexible sensor holder fastening said flexible sensor holder about a patient's extremity and holding said sensor relative to said patient's tissue.

22. The method of claim 21, wherein said locating step further comprises:
  routing a cable associated with said sensor through an access slot interconnecting said selected sensor holding recess to a lateral edge of said flexible sensor holder.

23. The method of claim 22, wherein said routing step further comprises selectively routing said cable to one of a front and rear lateral edge of said flexible sensor holder.

24. The method of claim 21, wherein said locating step further comprises:
  selectively attaching the sensor to said selected sensor holding recess.

25. The method of claim 24, wherein said attaching step comprises adhering said sensor to said selected sensor holding recess.

26. A flexible holder for positioning a sensor relative to selectable tissue regions on a patient, said holder comprising:
  a first flexible elongate member connectable about a patient's extremity;
  a second flexible elongate member connectable about a patient's extremity;
  an interconnecting member for interconnecting said first elongate member to said second elongate member; and
  at least first and second recesses located on an inside surface of at least one of said first and second elongate members for selectively receiving a sensor.

27. The flexible holder of claim 26, wherein said first and second elongate members each further comprise a connector for selectively connecting each said elongate member about a patient's extremity.

28. The flexible holder of claim 26, wherein said first and second elongate members are disposed relative to one another such that each said elongate member is connectable about separate portions of a patient's extremity.

29. The flexible holder of claim 28, wherein said first elongate member is connectable about a patient's extremity in a first plane and said second elongate member is connectable about a patient's extremity in a second plane.

30. The flexible holder of claim 29, wherein said first and second planes are transverse.

31. The flexible holder of claim 30, wherein one of said first and second elongate members is connectable about a patient's foot and the other of said first and second elongate members is connectable about a patient's leg.

32. The flexible holder of claim 26, wherein said first and second recesses are disposed in first and second positions on said first elongate member.

33. The flexible holder of claim 32, wherein said first and second recesses are disposed such that said recesses are capable of selectively holding a sensor relative to alternate regions of a patient's tissue when said holder is connected about said extremity.

34. The flexible holder of claim 26, wherein said first and second elongate members each contain at least one recess.

35. A method for providing a dual point connection for positioning a sensor relative to a tissue region on a patient, said method comprising the steps:
  positioning said flexible sensor holder relative to a patient's extremity;
  locating a sensor on a patient interface surface of said flexible sensor holder;
  first connecting said flexible sensor holder about a first portion of a patient's extremity;
  second connecting said flexible sensor holder about a second portion of the patient's extremity;
  selecting one of two provided sensor holding recesses operative to hold a sensor relative to first and second positions on a patient interface surface of said holder, wherein said first and second connecting steps fasten said flexible sensor holder about a patient's extremity and hold said sensor relative to said patient's tissue.

36. The method of claim 35, wherein said locating step further comprises locating said sensor in a sensor holding recess on a patient interface surface of said flexible sensor holder.

37. The method of claim 35, wherein said first and second connecting steps each further comprise:
  interconnecting a first portion of said flexible sensor holder to a second portion of said flexible sensor holder.

38. The method of claim 35, wherein said first and second connecting steps further comprise:
  first connecting said holder about said extremity in a first plane and second connecting said holder about said extremity in a second plane.

39. The method of claim 38, wherein said first and second planes are transverse.

40. The method of claim 38, wherein said first connection is about a patient's foot and said second connection is about a patient's ankle.

41. A convertible flexible sensor holder for providing a dual point connection to a patient's extremity in a first configuration and a single point connection to a patient's extremity in a second configuration, said holder comprising:
  a first flexible elongate member connectable about a first portion of a patient's extremity;
  a second flexible elongate member connectable about a second portion of a patient's extremity;
  at least two recesses located on an inside surface of at least one of said first and second elongate members for selectively receiving a sensor, wherein said recess positions said sensor relative to a patient's tissue upon connection of said elongate member to an extremity; and
  an interconnecting member having a first side attached to said first elongate member and a second side attached to said second elongate member, wherein at least one of said first and second attached sides is releasably attached such that at least one of said first and second elongate members is selectively disconnectable from said interconnecting member.

42. The flexible holder of claim 41, wherein an interface between said releasably attached side of said interconnecting member and said selectively disconnectable elongate member is perforated.

43. The flexible holder of claim 41, wherein said selectively disonnectable elongate member contains at least one of said two recesses.

44. A method for converting a dual connection sensor holder into a single connection sensor holder for holding a sensor relative to a patient's tissue, comprising the steps:
providing a dual connection sensor holder having first and second members for interconnecting about first and second portions of a patient's extremity, wherein at least one of said members contains a sensor holding recess on a patient interface surface;
determining for a particular sensor placement that a single connection sensor holder is preferable; and
detaching said member containing said sensor holding recess for use as a single connection sensor holder.

45. The method of claim 44, wherein said detaching step comprises tearing said member containing said sensor holding recess from said dual point connection sensor holder.

46. The method of claim 45, wherein said tearing step further comprises tearing along a perforated line.

47. A flexible holder for positioning a sensor relative to tissue region on a patient, said holder comprising:
a flexible elongate member having inside and outside surfaces, said elongate member conformable relative to a patient's extremity;
a first recess located on said inside surface for selectively receiving a sensor;
a first aperture associated with said first recess, said first aperture passing through said elongate member from said inside surface to said outside surface to provide access to said first recess through said elongate member; and
a connector for connecting said elongate member about a patient's extremity.

48. The flexible holder of claim 47, wherein said first aperture passes through at least a portion of said first recess.

49. The flexible sensor holder of claim 48, wherein said first recess is sized to receive a first portion of a sensor while a second portion of said sensor extends through said first aperture.

50. The flexible holder of claim 47, further comprising:
a second recess; and
a second aperture associated with said second recess, said second aperture passing through said elongate member.

51. The flexible sensor holder of claim 50, wherein said first and second recesses are sized to receive first and second portions of a sensor, respectively.

52. The flexible holder of claim 51, wherein said first and second recesses and first and second apertures combinatively secure a sensor relative to said flexible sensor holder.

53. The flexible sensor of claim 52, wherein a middle portion of said sensor is disposed on said elongate member's outside surface between said first and second apertures when said first and second sensor portions are recieved in said first and second recesses.

54. A flexible holder for positioning a sensor relative to tissue region on a patient, said holder comprising:
a compressible material layer having a compressible inside surface for interfacing with the tissue of a patient;
a backing layer releaseably laminated to at least a portion of an outside surface of said compressible material layer;
at least two recesses contained within said compressible material layer for selectively receiving a sensor; and
a connector for connecting said flexible holder to a patient.

55. The flexible sensor of claim 54, wherein said compressible material layer further comprises:
a plurality of one of loops and hooks affixed to said outside surface.

56. The flexible sensor of claim 55, wherein said backing layer comprises an inside surface having a plurality of one of loops and hooks and an outside surface having the other of a plurality of hooks and loops.

57. The flexible sensor of claim 56, wherein a portion of said backing layer inside surface is operable to engage a portion of said backing layer outside surface when said flexible holder is disposed about a patient's extremity.

58. The flexible sensor of claim 57, wherein said hooks and loops form said connector for securing said flexible holder about a patient's extremity.

59. A method for positioning a sensor relative to a tissue region on a patient, said method comprising the steps:
positioning a flexible sensor holder relative to patient's tissue;
cutting at least a first layer of said flexible sensor holder to a desired length;
locating a sensor into one of at least two sensor holding recesses on said flexible sensor holder;
connecting said flexible sensor holder about a patient's extremity.

60. The method of claim 59, wherein said cutting step further comprises:
delaminating at least a first layer of said flexible sensor from at least a second layer;
cutting at least one of said first and second layers to a desired length; and
re-laminating said first and second layers.

61. The method of claim 59, wherein said locating step includes positioning a portion of said sensor through an aperture associated with said recess.

* * * * *

UNITED STATES PATENT AND TRADEMARK OFFICE
CERTIFICATE OF CORRECTION

PATENT NO. : 7,190,987 B2 Page 1 of 1
APPLICATION NO. : 10/394525
DATED : March 13, 2007
INVENTOR(S) : Lindekugel et al.

It is certified that error appears in the above-identified patent and that said Letters Patent is hereby corrected as shown below:

<u>Title Page</u>
Item (56) References Cited, delete "RE360,000" and insert therefor --RE36,000--.

<u>Column 17 Claim 43</u>
Line 2, delete "disonnectable" and insert therefor --disconnectable--.

<u>Column 18 Claim 53</u>
Line 2, delete "recieved" and insert therefor --received--.

Signed and Sealed this

Fifteenth Day of May, 2007

JON W. DUDAS
*Director of the United States Patent and Trademark Office*